(12) United States Patent
Marraccini et al.

(10) Patent No.: US 6,841,662 B2
(45) Date of Patent: Jan. 11, 2005

(54) COFFEE MANNANASE

(75) Inventors: Pierre Marraccini, Savonnieres (FR); John Rogers, St. Cyr-Sur-Loire (FR)

(73) Assignee: Nestec S.A., Vevey (CH)

( * ) Notice: Subject to any disclaimer, the term of this patent is extended or adjusted under 35 U.S.C. 154(b) by 188 days.

(21) Appl. No.: 09/850,982

(22) Filed: May 8, 2001

(65) Prior Publication Data

US 2002/0166145 A1 Nov. 7, 2002

Related U.S. Application Data

(63) Continuation of application No. PCT/EP99/08314, filed on Oct. 28, 1999.

(30) Foreign Application Priority Data

Nov. 9, 1998 (EP) .............................. 98203742

(51) Int. Cl.[7] .......................... C12N 1/00; C12N 15/00; C12N 15/09; C12N 15/63; C12N 15/74
(52) U.S. Cl. .................... 536/23.6; 536/23.1; 536/23.2; 435/243; 435/320.1; 435/252.3
(58) Field of Search .............................. 435/252.3, 200, 435/209, 3, 183, 195, 410, 113, 440, 243, 320.1; 800/278, 284, 298; 536/23.1, 23.2, 23.6

(56) References Cited

U.S. PATENT DOCUMENTS

| 5,714,183 A | 2/1998 | Nicolas et al. ................. 426/45 |
| 5,795,764 A | * 8/1998 | Christgau ................... 435/200 |

FOREIGN PATENT DOCUMENTS

| WO | WO 95 06478 A | 3/1995 |
| WO | WO 97/20937 | * 6/1997 | ........... C12N/15/56 |
| WO | WO 98/06852 | * 2/1998 | ........... C12N/15/52 |

OTHER PUBLICATIONS

GenBank Accession number AFO1744 submitted Aug. 5, 1997.*
Fourgoux–Nicol et al., 1999, Plant Molecular Biology, vol. 40; pp. 857–872.*
Broun P. et al. Science vol. 282; Nov. 13, 1998, pp. 1315–1317.*
Sweetlove L. et al., Biochem J., 1996; vol. 320; pp. 493–498.*
Science, Jan. 25, 2002; vol. 295, pp. 604–604.*
Morten Joersbo et al., "In vivo modification of the cell wall polysaccharide galactomannan of guar transformed with a a–galactosidase gene cloned from senna", Molecular Breeding 7: pp. 211–219 (2001).
Abstract XP002098585 of J. F. Giorgini et al., "Effect of Embryo and exogenous GA3 on endospermic endo–beta–mannanase activity of *Coffea Arabica* L. during germination and early seedling growth", vol. 125, No. 3, (1996).
XP–002095786 of J. D. Bewley et al., Molecular cloning of a cDNA encoding a (1→4)–β–mannan endohydrolase from the seeds of germinated tomato (*Lycopersicon esculentum*) PLANTA, vol. 203, pp. 454–459 (1997).

* cited by examiner

*Primary Examiner*—David T. Fox
*Assistant Examiner*—Russell Kallis
(74) *Attorney, Agent, or Firm*—Winston & Strawn LLP

(57) ABSTRACT

A DNA fragment derived from coffee encoding at least one enzyme involved in the hydrolysis of polysaccharides comprising pure or branched mannan molecules linked to each other via a β (1→4) linkage.

13 Claims, 4 Drawing Sheets

SEQUENCE LISTING

<160> NUMBER OF SEQ ID NOS: 12

<210> SEQ ID NO 1
<211> LENGTH: 1613
<212> TYPE: DNA
<213> ORGANISM: Coffea arabica

<400> SEQUENCE: 1

```
ttcattaaaa atggccttct ccaggagaag caatatcagc aacttctctt gctgcttcct      60
tgtgatcatc gtcttatccc tgcattgcga aaatcatata gtttcttctt ctgcttcgcg     120
ctttattcaa acaagaggaa cccgattcgt gttaggtggc tacccatttt ttttcaatgg     180
gttcaactcc tactggatga tgcatgttgc agctgagcca agtgaaaggc ataaaatttc     240
caatgtattt cgcgaggctg ctgctacagg gcttactgtt tgccggacat gggcattcag     300
cgatggtggc gatcgagctc ttcaaatgtc ccccggagtc tatgatgaac gtgtctttca     360
ggcccttgat tttgtggtat cggaagcaag gaagtatgga gttcacttaa tcctgagtct     420
gaccaacaac tacaaggact ttggaggaag gacgcaatac gtgacgtggg ctaaaaatgc     480
cggagtacaa gtgaatagcg atgatgattt ttacaccaag aatgctgtca agggatatta     540
caagaatcac attaagaaag tgttgactag gatcaacaca atcagtagag ttgcatataa     600
agatgatcca acagtcatgg catgggagct aataaatgaa cctcgttgcc aggtcgactt     660
ctccggaaaa accttaaatg cttgggttca agaaatggca acttacgtca aatcactcga     720
taacaaacac cttctagaaa taggcatgga gggattctac ggagattcaa tgccaggcaa     780
aaagcagtac aatcctggat accagtggg cacagatttt atcaccaata atcttatcaa     840
agagatagat tttgcaacca ttcatgcata tcccgatatt tggctgtctg gacagagcga     900
cggtgcacag atgatgttca tgagaaggtg gatgaccagt cactccacag actctaagac     960
catacttaaa aaaccattgg ttctcgctga atttgggaaa tcaagtaaag atccaggata    1020
cagtttatat gccagggagt cattcatggc cgcaattac ggtgatatct acaggtttgc    1080
```

-continued

```
tagaagagga ggcattgcag gtggattggt ttggcaaatc ctggccgagg gaatgcaacc    1140
gtacgcagat gggtatgaaa ttgtcttgtc tcagaaccca tcaaccggac gaatcataag    1200
ccaacagtct cgacaaatga cttcactcga ccatatgagc agtaatagaa ccaattctca    1260
aagcaacaaa ctgcgcaatt caaggagca gtgatcagtc ttccagaaag tctacttgag    1320
tttgttcgta tgtcaaaatc aagtatcaac catagaaatt tccattatat tcggagtgtt    1380
ttagtcaagt tctagtaata ccgctggagt catgatagtt atgacagtaa taccgctgga    1440
gtcaagttct agtaataccg ttggagtcaa gttatgatag ttatttaaaa attagtattt    1500
tattacaaat ttgttattgt gtgagacttg tttattaagt aaatggaaaa gtcttatcat    1560
tattatcatt tgagaaaaaa aaaaaaaaaa aaaaaaaaaa aaaaaaaaaa aaa           1613
```

```
<210> SEQ ID NO 2
<211> LENGTH: 427
<212> TYPE: PRT
<213> ORGANISM: Coffea arabica

<400> SEQUENCE: 2

Met Ala Phe Ser Arg Arg Ser Asn Ile Ser Asn Phe Ser Cys Cys Phe
1               5                   10                  15

Leu Val Ile Ile Val Leu Ser Leu His Cys Glu Asn His Ile Val Ser
            20                  25                  30

Ser Ser Ala Ser Arg Phe Ile Gln Thr Arg Gly Thr Arg Phe Val Leu
        35                  40                  45

Gly Gly Tyr Pro Phe Phe Asn Gly Phe Asn Ser Tyr Trp Met Met
    50                  55                  60

His Val Ala Ala Glu Pro Ser Glu Arg His Lys Ile Ser Asn Val Phe
65                  70                  75                  80

Arg Glu Ala Ala Ala Thr Gly Leu Thr Val Cys Arg Thr Trp Ala Phe
                85                  90                  95

Ser Asp Gly Gly Asp Arg Ala Leu Gln Met Ser Pro Gly Val Tyr Asp
            100                 105                 110

Glu Arg Val Phe Gln Ala Leu Asp Phe Val Val Ser Glu Ala Arg Lys
        115                 120                 125

Tyr Gly Val His Leu Ile Leu Ser Leu Thr Asn Asn Tyr Lys Asp Phe
    130                 135                 140

Gly Gly Arg Thr Gln Tyr Val Thr Trp Ala Lys Asn Ala Gly Val Gln
145                 150                 155                 160

Val Asn Ser Asp Asp Phe Tyr Thr Lys Asn Ala Val Lys Gly Tyr
                165                 170                 175

Tyr Lys Asn His Ile Lys Lys Val Leu Thr Arg Ile Asn Thr Ile Ser
            180                 185                 190

Arg Val Ala Tyr Lys Asp Asp Pro Thr Val Met Ala Trp Glu Leu Ile
        195                 200                 205

Asn Glu Pro Arg Cys Gln Val Asp Phe Ser Gly Lys Thr Leu Asn Ala
    210                 215                 220

Trp Val Gln Glu Met Ala Thr Tyr Val Lys Ser Leu Asp Asn Lys His
225                 230                 235                 240

Leu Leu Glu Ile Gly Met Glu Gly Phe Tyr Gly Asp Ser Met Pro Gly
                245                 250                 255

Lys Lys Gln Tyr Asn Pro Gly Tyr Gln Val Gly Thr Asp Phe Ile Thr
            260                 265                 270

Asn Asn Leu Ile Lys Glu Ile Asp Phe Ala Thr Ile His Ala Tyr Pro
```

-continued

```
            275                 280                 285
Asp Ile Trp Leu Ser Gly Gln Ser Asp Gly Ala Gln Met Met Phe Met
        290                 295                 300

Arg Arg Trp Met Thr Ser His Ser Thr Asp Ser Lys Thr Ile Leu Lys
305                 310                 315                 320

Lys Pro Leu Val Leu Ala Glu Phe Gly Lys Ser Ser Lys Asp Pro Gly
                325                 330                 335

Tyr Ser Leu Tyr Ala Arg Glu Ser Phe Met Ala Ala Ile Tyr Gly Asp
            340                 345                 350

Ile Tyr Arg Phe Ala Arg Arg Gly Gly Ile Ala Gly Gly Leu Val Trp
        355                 360                 365

Gln Ile Leu Ala Glu Gly Met Gln Pro Tyr Ala Asp Gly Tyr Glu Ile
    370                 375                 380

Val Leu Ser Gln Asn Pro Ser Thr Gly Arg Ile Ile Ser Gln Gln Ser
385                 390                 395                 400

Arg Gln Met Thr Ser Leu Asp His Met Ser Ser Asn Arg Thr Asn Ser
                405                 410                 415

Gln Ser Asn Lys Leu Arg Asn Ser Lys Glu Gln
            420                 425
```

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotides provided by
    Eurogentec (Parc Scientifique due Sart Tilman [Sart Tilman
    Scientific Park]-4102 Seraing-Belguim).
<220> FEATURE:
<221> NAME/KEY: misc_feature
<222> LOCATION: (3)..(3)
<223> OTHER INFORMATION: a or c or g or t/u
<220> FEATURE:
<221> NAME/KEY: misc_feature
<222> LOCATION: (12)..(12)
<223> OTHER INFORMATION: a or c or g or t/u

<400> SEQUENCE: 3
ggnatggarg gnttytaygg                                           20

<210> SEQ ID NO 4
<211> LENGTH: 15
<212> TYPE: DNA
<213> ORGANISM: Artificial Sequence
<220> FEATURE:
<223> OTHER INFORMATION: Synthetic oligonucleotides provided by
    Eurogentec (Parc Scientifique due Sart Tilman [Sart Tilman
    Scientific Park]-4102 Seraing-Belguim).

<400> SEQUENCE: 4
tttttttttt ttttt                                                15

<210> SEQ ID NO 5
<211> LENGTH: 17
<212> TYPE: DNA
<213> ORGANISM: Artificial Sequence
<220> FEATURE:
<223> OTHER INFORMATION: Synthetic oligonucleotides provided by
    Eurogentec (Parc Scientifique due Sart Tilman [Sart Tilman
    Scientific Park]-4102 Seraing-Belguim).

<400> SEQUENCE: 5
aaatctgtgc ccacttg                                              17

```
<210> SEQ ID NO 6
<211> LENGTH: 17
<212> TYPE: DNA
<213> ORGANISM: Artificial Sequence
<220> FEATURE:
<223> OTHER INFORMATION: Synthetic oligonucleotides provided by
      Eurogentec (Parc Scientifique due Sart Tilman [Sart Tilman
      Scientific Park]-4102 Seraing-Belguim).

<400> SEQUENCE: 6
gtaaaacgac ggccagt                                                    17

<210> SEQ ID NO 7
<211> LENGTH: 17
<212> TYPE: DNA
<213> ORGANISM: Artificial Sequence
<220> FEATURE:
<223> OTHER INFORMATION: Synthetic oligonucleotides provided by
      Eurogentec (Parc Scientifique due Sart Tilman [Sart Tilman
      Scientific Park]-4102 Seraing-Belguim).

<400> SEQUENCE: 7
caggaaacag ctatgac                                                    17

<210> SEQ ID NO 8
<211> LENGTH: 21
<212> TYPE: PRT
<213> ORGANISM: Coffea arabica
<220> FEATURE:
<221> NAME/KEY: MISC_FEATURE
<222> LOCATION: (16)..(16)
<223> OTHER INFORMATION: variable

<400> SEQUENCE: 8

Ser Phe Asn Phe Val Lys Thr Arg Gly Thr Glu Phe Val Met Asp Xaa
1               5                   10                  15

Arg Phe Leu Tyr Leu
            20

<210> SEQ ID NO 9
<211> LENGTH: 10
<212> TYPE: PRT
<213> ORGANISM: Coffea arabica

<400> SEQUENCE: 9

Thr Trp Ala Phe Ser Asp Gly Gly Tyr Arg
1               5                   10

<210> SEQ ID NO 10
<211> LENGTH: 17
<212> TYPE: PRT
<213> ORGANISM: Coffea arabica

<400> SEQUENCE: 10

Glu Tyr Asn Pro Gly Tyr Gln Val Gly Thr Asp Phe Ile Ser Asn Asn
1               5                   10                  15

Arg

<210> SEQ ID NO 11
<211> LENGTH: 36
<212> TYPE: DNA
<213> ORGANISM: Artificial Sequence
<220> FEATURE:
<223> OTHER INFORMATION: Synthetic oligonucleotides provided by
      Eurogentec (Parc Scientifique due Sart Tilman [Sart Tilman
      Scientific Park]-4102 Seraing-Belguim).
```

-continued

```
<400> SEQUENCE: 11
gtcttatccc tggatcccga aaatcatata gtttct                    36

<210> SEQ ID NO 12
<211> LENGTH: 40
<212> TYPE: DNA
<213> ORGANISM: Artificial Sequence
<220> FEATURE:
<223> OTHER INFORMATION: Synthetic oligonucleotides provided by
      Eurogentec (Parc Scientifique due Sart Tilman [Sart Tilman
      Scientific Park]-4102 Seraing-Belguim).

<400> SEQUENCE: 12
gtactctgca gactttctgg aagactgatc actgctcctt                40
```

COFFEE MANNANASE

CROSS-REFERENCE TO RELATED APPLICATION

This application is a continuation of the U.S. National Stage designation of International application PCT/EP99/08314 filed Oct. 28, 1999, the content of which is expressly incorporated herein by reference thereto.

FIELD OF THE INVENTION

The present invention relates to the use of fragments of coffee DNA encoding at least one enzyme involved in the hydrolysis of polysaccharides consisting at least of simple or branched mannan molecules linked to each other via a β (1→4) linkage.

BACKGROUND ART

Polysaccharides which contain mannose are frequently present in the cell walls of higher plants, in particular in leguminous plants, and are considered to be a carbohydrate store in the seeds.

In several plants, it has been shown that endo-β-mannanase activity is mainly detected in the endosperm of seeds undergoing germination (Bewley, Trends Plant Sci 2, 464–469, 1997).

In the coffee bean, galactomannans in particular are found. The latter represent approximately 24% of the dry weight of the bean (Bradbury and Halliday, J Agric Food Chem 38, 389–392, 1990). These polysaccharides consist of a linear chain of mannosyl residues which are linked to each other via β-1→4 type linkages and to which are attached α-galactosyl residue monomers. It is also known that the enzyme named endo-β-mannanase (E.C 3.2.1.78) is a hydrolase which degrades (1→4)-β-mannan polymers, thus facilitating the exit of the rootlet during germination and releasing small oligosaccharides which are then used as a source of energy for the growth of the young plant.

In industrial processes, during the treatment of coffee, the mannan molecules and their derivatives constitute a considerable portion of the insoluble sediments. In addition, the fraction of these molecules which dissolves during the first extraction (approximately 50%) is also very poorly soluble, and is therefore responsible for the majority of the secondary precipitations which occur during the subsequent steps. In patent EP 0676145A, therefore, it has been demonstrated that it is possible to hydrolyse coffee galactomannans using an immobilized mannanase extracted from *Aspergillus niger*.

Thus no gene or group of genes encoding at least one enzyme derived from coffee, which enzyme is involved in the hydrolysis of polysaccharides consisting at least of simple or branched mannan molecules linked to each other via a β (1→4) linkage has so far been identified and/or sequenced.

It would, therefore, be advantageous to isolate such enzymes derived from the coffee bean.

SUMMARY OF THE INVENTION

The present invention now provides a novel means for controlling, modifying and/or restoring the hydrolysis of coffee polysaccharides consisting at least of simple or branched mannan molecules linked to each other via a β (1→4) linkage. To this effect, the present invention relates to any fragment of DNA derived from coffee encoding at least one enzyme involved in the hydrolysis of such polysaccharides.

The present invention also relates to the use of all or part of such fragments of DNA as a primer for carrying out a PCR or as a probe for detecting, in vitro, or modifying, in vivo, at least one coffee gene encoding at least one endo-β-mannanase.

The present invention also relates to any protein derived from the coffee bean, which is encoded by a coffee gene and involved in the hydrolysis of polysaccharides consisting at least of simple or branched mannan molecules linked to each other via a β (1→4) linkage, and which has the amino acid sequence SEQ ID NO: 2 or any amino acid sequence homologous to the latter.

Another subject of the invention relates to any microorganism and any plant cell comprising, integrated into its genome or by means of a plasmid which can replicate, a fragment of DNA according to the present invention.

Finally, the invention relates to a dietary, cosmetic or pharmaceutical composition comprising a fragment of DNA or a protein according to the invention.

BRIEF DESCRIPTION OF THE FIGURES

Preferred embodiments of the invention are now illustrated in the following drawing figures, wherein.

DETAILED DESCRIPTION OF THE INVENTION

Figure 1:
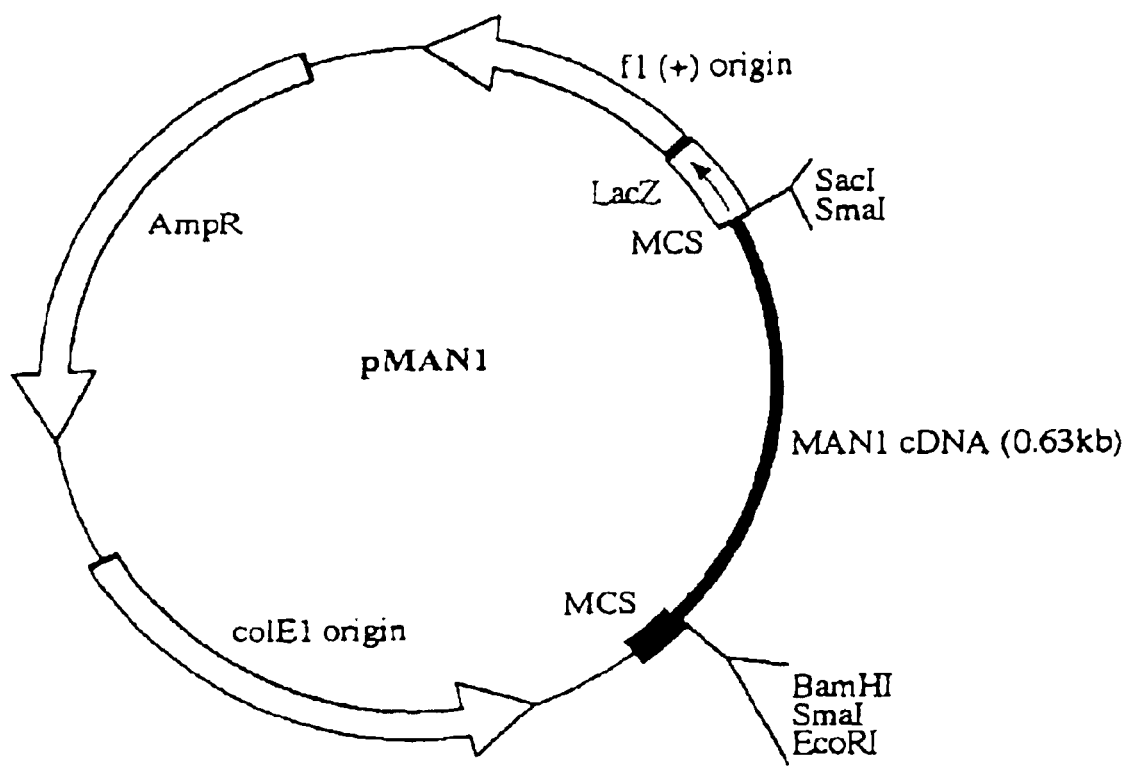
FIG. 1 represents the 3.58 kb plasmid pMAN1.

For the purposes of the present invention, the term "homologous sequence" is intended to mean any nucleic acid or amino acid sequence having an identical function, which differs from the sequences according to the invention only by the substitution, deletion or addition of a small number of nucleic acid bases or of amino acids, for example 1 to 500 base pairs (bp) or 1 to 150 amino acids.

In this context, two DNA sequences which, because of the degeneracy of the genetic code, encode the same polypeptide will in particular be considered to be homologous. Similarly, two functional proteins which are recognized by the same antibody, the ratio of the values of intensity of recognition of the two proteins by the antibody not exceeding 100, for example, will be considered to be homologous.

Also considered to be a homologous sequence will be that sequence which has more than 70% homology with the sequences according to the invention, in particular more than 80% or 90%. In the latter case, the homology is determined by the ratio between the number of bases or of amino acids of a homologous sequence which are identical to those of a sequence according to the invention, and the total number of bases or of amino acids of said sequence according to the invention.

For the purposes of the present invention, the term "fragment which hybridizes" is intended to mean any fragment capable of hybridizing to the fragments according to the invention by the method of Southern Blot (Sambrook et al., Molecular Cloning, A Laboratory Manual, Cold Spring Harbor Laboratory Press, USA, 1989, chapters 9.31 to 9.58). Preferably, the hybridization is carried out under stringent conditions so as to avoid aspecific or relatively unstable hybridizations.

Finally, the term "fragment" or "fragment of DNA" should be understood to be a double-stranded DNA of chromosomal origin which can be synthesized, reproduced in vitro for example by the known method termed "Polymerase Chain Reaction", or reproduced in vivo in a bacterium of the *Escherichia coli* type, for example.

In the remainder of the description, the sequences SEQ ID NO: refer to the sequences given in the sequence listing hereinafter. The synthetic oligonucleotides SEQ ID NO: 3 to SEQ ID NO: 7, and SEQ ID NO: 11 to SEQ ID NO: 12 mentioned in the description and given in the sequence listing hereinafter are provided by Eurogentec (Parc Scientifique du Sart Tilman [Sart Tilman Scientific Park]-4102 Seraing-Belgium).

It has been possible to characterize a 1613 bp DNA sequence derived from coffee. Thus, the present invention relates to any fragments of DNA derived from coffee encoding at least one enzyme involved in the hydrolysis of polysaccharides consisting at least of pure or branched mannan molecules linked to each other via a β (1→4) linkage.

The fragment of DNA derived from coffee according to the invention preferably encodes at least one endo-β-mannanase.

It has been possible to show that all or part of the sequence SEQ ID NO: 1 makes it possible, subsequent to a transformation, to hydrolyse polysaccharides consisting at least of pure or branched mannan molecules linked to each other via a β (1→4) linkage in a host cell, such as a plant cell or a microorganism.

Taking into account the advantage of the present invention, the invention relates to any fragment of DNA having the nucleic acid sequence SEQ ID NO: 1 or any fragment of DNA which is homologous to or hybridizes to this nucleic acid sequence. Preferably, the invention relates to the fragment of DNA delimited by nucleotides 11 to 1294 of the nucleic acid sequence SEQ ID NO: 1.

Thus, the invention also relates to the novel enzymes encoded by the genes of the sequence SEQ ID NO: 1, in particular the sequences which are homologous to them. It is thus possible to envisage using them to modify or degrade such polysaccharides in vitro, for example. For this, it is preferable to purify at least one of these enzymes, by conventionally over-expressing their gene in a bacterium and isolating them conventionally, by precipitation and/or chromatography If of the culture medium, for example.

The invention also relates to the use of all or part of fragments of DNA. Use can be made, in particular, of all or part of fragments of DNA according to the invention, of at least 10 bp as a primer for carrying out a PCR or as a probe for detecting, in vitro, or modifying, in vivo, at least one coffee gene encoding at least one endo-β-mannanase.

Moreover, a subject of the present invention is also a protein derived from the coffee bean, which is encoded by a coffee gene and involved in the hydrolysis of polysaccharides consisting at least of pure or branched mannan molecules linked to each other via a β (1→4) linkage, and which has the amino sequence SEQ ID NO: 2 or any amino acid sequence homologous to the latter. The endo-β-mannanase can contain at least one of the following amino acid sequences: SEQ ID NO: 8 to 10.

Another subject of the present invention relates to process for hydrolysing polysaccharides consisting at least of pure or branched mannan molecules linked to each other via a β (1→4) linkage, in which (1) a fragment of DNA encoding the enzymes according to the invention is cloned into a vector, said vector also comprising a sequence allowing autonomous replication or integration in a host cell, (2) a hose cell is transformed with said vector, and then (3) the transformed host cell is cultured under conditions suitable for the hydrolysis of such polysaccharides.

The present invention therefore opens up the possibility of using fragments of DNA according to the invention to modify the production of polysaccharides consisting at least of pure or branched mannan molecules linked to each other via a β (1→4) linkage in a host cell, in particular a coffee bean cell. It is thus possible to envisage expressing or over-expressing DNAs according to the invention, in a coffee bean cell, in order to produce such polypeptides intended to modify the aroma and the structure of the coffee beans, for example.

The present invention also makes it possible to have novel means for identifying coffee genes involved in the hydrolysis of polysaccharides consisting at least of pure or branched mannan molecules linked to each other via a β (1→4) linkage.

Finally, the present invention also provides novel enzymes involved in the hydrolysis of such polysaccharides. These enzymes can thus be advantageously used to synthesize or modify such polysaccharides, in vitro.

The present invention also relates to a plant cell comprising, integrated into its genome or by means of a recombinant vector, a fragment of DNA encoding at least one enzyme involved in the hydrolysis of polysaccharides consisting at least of pure or branched mannan molecules linked to each other via a β (1→4) linkage. Preferably, this plant cell comprises a fragment of DNA having the nucleotide sequence SEQ ID NO: 1, or a fragment of DNA having a nucleic acid sequence which is homologous to or hybridizes to the nucleic acid sequence SEQ ID NO: 1, or a fragment of DNA comprising at least nucleotides 11 to 1294 of the nucleic acid sequence SEQ ID NO: 1.

Preferably, this plant cell is a coffee cell. It is possible in particular to choose, as coffee cells, cells derived from a plant of *Coffea canephora* var. *robusta*, *Coffea arabica* or any other species of the Coffea genus.

The present invention also relates to any plant or any seed consisting of plant cells comprising, integrated into its genome or by means of a recombinant vector, a fragment of DNA encoding at least one enzyme involved in the hydrolysis of polysaccharides consisting at least of pure or branched mannan molecules linked to each other via a β (1→4) linkage.

Any microorganism comprising, integrated into its genome or by means of a plasmid which can replicate, a fragment of DNA according to the invention such that it expresses at least one enzyme involved in the hydrolysis of polysaccharides consisting at least of pure or branched mannan molecules linked to each other via a β (1→4) linkage is also a subject of the present invention.

Another subject of the invention relates to any dietary, cosmetic or pharmaceutical composition comprising a fragment of DNA according to the invention or a protein according to the invention.

Finally, the present invention relates to a process for treating coffee beans, in which all or part of the protein according to the invention is used. It is in particular possible to use all or part of the protein according to the invention to increase the percentage of solids extracted, during the treatment of coffee beans. Using all or part of the protein according to the invention, it is thus possible to increase the extraction yield while at the same time decreasing the amount of sediment.

After over-expression of the fragment of DNA according to the invention in a microorganism, in a fungus or in an undifferentiated plant cell, the sediments can be treated with the more or less purified enzyme, so as to thus increase the extraction yields.

After over-expression of the fragment of DNA according to the invention in a microorganism, in a fungus or in an undifferentiated plant cell, it is also possible to treat the coffee liquor, so as to decrease the sedimentation due to the mannans which gel.

EXAMPLES

The present invention is described in more detail hereinafter with the aid of the further description which will follow and which refers to examples of production of fragments of DNA, of recombinant plasmids and of transformed bacteria according to the invention. It goes without saying, however, that these examples are given by way of illustration of the subject of the invention for which they in no way constitute a limitation. The handling of the DNA, the cloning and the transformation of bacterial cells are, in the absence of instructions to the contrary, carried out according to the protocols described in the manual by Sambrook et al, mentioned above. The percentages are given by weight, unless otherwise indicated.

Example 1

Isolation of the Coffee endo-β-mannanase cDNA 1.1 Isolation of the Total RNAs and of the Poly A+ Messenger RNAs from the Germinating Coffee Bean Coffee beans (*Coffea arabica* var. *caturra* 2308) are harvested at the mature stage, depulped immediately and dried for three days at room temperature. Next, the parchment skin of the beans is removed, and they are dried and then sterilized in order to be germinated in culture in vitro. To do this, they are placed in Rovral (0.12% v/v) for 1 hour, rinsed with sterile water, placed in a solution of calcium hypochlorite (6% w/v) to which a few drops of Teepol emulsifier are added, for 1 hour, and then rinsed 4 times with sterile water before being cultured in test-tubes on an agar-water medium. The germination occurs at 25° C. in the presence of light. The moment when the beans are placed on the agar bed is considered to be day after soaking zero (DAS=0).

The total RNAs of beans are extracted after 22 days of germination (days after soaking in water DAS 22).

To do this, the bean is rapidly ground in liquid nitrogen and the powder obtained is resuspended in 8 ml of buffer at pH 8.0 containing 100 mM Tris HCl, 0.1% w/v of SDS and 0.5% v/v of β-mercaptoethanol, it is homogenized with one volume of phenol saturated with 100 mM Tris HCl, pH 8.0, and then it is centrifuged at 12 000 g for 10 min at 4° C., so as to extract the aqueous phase, which is centrifuged (i) once with an equivalent volume of phenol, (ii) twice with an equivalent volume of phenol:chloroform (1:1) and (iii) twice with an equivalent volume of chloroform.

The total nucleic acids are then precipitated for 1 h at −20° C. by adding to the aqueous phase $\frac{1}{10}$ of a volume of 3 M sodium acetate, pH 5.2, and 2.5 volumes of ethanol.

The resulting mixture is then centrifuged at 12 000 g for 30 min at 4° C., and the pellet is taken up in 10 ml of $H_2O$, before re-precipitating the nucleic acids in the presence of LiCl (2 M final) and of ethanol (2.5 volumes).

After centrifugation, the pellet of total RNAs is taken up in 1 ml of $H_2O$ and it is digested for 1 h at 37° C. with RQ1 DNAse (Promega Corporation, 2800 Woods Hollow Road, Madison, Wis. 53711 USA) in order to eliminate any trace of DNA, and then the total RNAs are deproteinated by treating with phenol and with chloroform, before precipitating them in the presence of sodium acetate as described above.

The total RNAs are then taken up in 500 µl of $H_2O$, and they are quantified by spectrophotometric assay at 260 nm. Their quality is analysed by agarose gel electrophoresis in the presence of formaldehyde.

To do this, the poly A+ messenger RNAs (mRNAs) are then purified from 500 µg of total RNAs using the Oligotex-dT purification system (Qiagen INC., 9600 De Soto Avenue, Chatsworth, Calif., 91311 USA), and then the quantity of messenger RNAs is evaluated using the DNA Dipstick kit (InVitrogen BC, De Schelp 12, 9351 NV Leek, the Netherlands).

1.2. Construction and Screening of the cDNA Library

The synthesis of complementary DNA (cDNA), required for constructing the libraries, is carried out according to the recommendations supplied in the "Riboclone cDNA synthesis system M-MLV (H-)" kit (Promega, USA), except for the EcoRI linker ligation step. This makes it possible to clone these cDNAs directly into the vector pPCR-Script Amp SK(+) (Stratagene, 11011 North Torrey Pines Road, La Jolla, Calif. 92037, USA). The efficiency of this cDNA synthesis reaction is monitored by adding alpha-($^{32}$P)-dCTP during the synthesis of the two DNA strands.

After migration on alkaline agarose gel (Sambrook et al., 1989), the length of the neosynthesized cDNAs is estimated as ranging from 0.2 to more than 4.3 kb. The quantifications, using the DNA Dipstick kit (InVitrogen BV, De Schelp 12, 93 51 NV Leek, the Netherlands), show that approximately 100 ng of cDNA are synthesized from 1 µg of mRNA.

The cDNAs ligated into the vector pPCR-Script Amp SK(+) (Stratagene, USA) were used to transform the *Escherichia coli* strain XL2-Blue MRF' (Stratagene, USA). The bacteria which contain recombinant vectors are selected on plates of LB (Luria-Bertani) medium containing 20 µg.ml$^{-1}$ of ampicillin, and 80 µg.ml$^{-1}$ of methicillin, and in the presence of IPTG and of X-Gal (Sambrook et al., 1989). They are then cultured on petri dishes, so as to obtain approximately 300 clones per dish. These clones are transferred onto a Nylon filter and they are then treated according to the recommendations provided by Boehringer Mannheim (Boehringer Mannheim GmbH, Biochemica, Postfach 310120, Mannheim 31, Del.). The plasmids of this cDNA library are also extracted from an overnight culture of these transformants, in the presence of 25 ml of LB medium containing 50 µg.ml$^{-1}$ of ampicillin, and using the "QiaFilter Plasmid MidiKit" (Qiagen INC., USA).

1.3. Isolation of the cDNA Encoding the Coffee Endo-β-mannanase

In a preliminary experiment, the synthesis of the first strand of cDNA is carried out according to the recommendation supplied in the "Riboclone cDNA synthesis system M-MLV (H-)" kit (Promega, USA). The efficiency of this reaction is monitored by adding alpha-($^{32}$P)-dCTP during the cDNA synthesis.

The synthesis of the second strand of the cDNA is then carried out by performing an RT (Reverse Transcription)-PCR reaction (U.S. Pat. No. 4,683,195 and U.S. Pat. No. 4,683,202) using the synthetic oligonucleotide MAN 2, having the nucleic acid sequence SEQ ID NO: 3, and the synthetic oligonucleotide DT15, having the nucleic acid sequence SEQ ID NO: 4. The synthetic oligonucleotide MAN 2 corresponds to the amino acid sequence situated between amino acids 206 and 212 of the protein sequence of *Lycopersicon esculentum* (Bewley et al., Planta 203, 454–459, 1997) which is also conserved in the endo-β- mannanase protein sequences of *Trichoderma reesei* (Stalbrand et al., GenBank Accession Number L25310, 1993) and *Aspergillus aculeatus* (Christgau et al., Biochem Mol Biol Internat 33, 917–925, 1994).

The PCR reaction is carried out in the presence of 1 to 10 ng of first strand of cDNA, in a final volume of 50 µl containing 50 mM KCl, 10 mM Tris-HCl, pH 8.8, 1.5 mM $MgCl_2$, 0.1 mg.$ml^{-1}$ gelatin, 0.2 mM of each dNTP, 0.25 µM of each oligonucleotide (MAN 2 and DT15) and 3 units of Taq DNA polymerase (Stratagene, USA). The reaction mixture is covered with 50 µl of mineral oil and incubated for 35 cycles (94° C.-30 s, 45° C.-30 s, 72° C.-3 min) followed by a final extension at 72° C. for 7 min. At the end of this reaction, a majority PCR product approximately 600 bp long is obtained, which was purified on electrophoresis gel using the "Gel Nebulizer-Micropure 0.22 µm" DNA extraction system (Amicon INC., 72 Cherry Hill Drive, Beverly, Mass. 01915 USA). This fragment is treated with Pfu DNA polymerase (Stratagene, USA) in order to convert its sticky ends to blunt ends. This reaction takes place in a final volume of 13 µl containing approximately 200 ng of DNA fragment, 1 mM of dNTP, 10 mM KCl, 6 mM $(NH_4)_2SO4$, 20 mM Tris-HCl, pH 8.0, 0.1% Triton X-100, 2 mM $MgCl_2$, 10 µg.$ml^{-1}$ PSA and 2.5 units of Pfu DNA polymerase, The reaction mixture is covered with 20 µl of oil, and this is incubated at 72° C. for 30 min. The mixture obtained is desalified on a Microcon 50 cartridge (Amicon INC., USA) and ligated into the vector pPCR-Script Amp SK(+) (Stratagene, USA).

For this, 50 ng of PCR fragment are added to a ligation mixture which comprises 10 mM KCl, 6 mM $(NH_4)_2SO4$, 20 mM Tris-HCl, pH 8, 0.1% Triton X-100, 2 mM $MgCl_2$, 10 µg.$ml^{-1}$ BSA, 10 ng of the cloning vector pPCR-Script SK(+), 5 units of the SfrI restriction enzyme, 4 units of T4 DNA ligase and 5 mM of rATP. This reaction is incubated for 60 min. at 25° C. and is then used to transform the *Escherichia coli* strain XL2-Blue MRF' (Stratagene, USA). The bacteria which contain recombinant vectors are selected on plates of LB medium containing 20 µg.$ml^{-1}$ of ampicillin, and 80 µg.$ml^{-1}$ of methicillin, and in the presence of IPTG and of X-Gal (Sambrook et al., 1989).

At the end of the transformation, a clone was isolated which harbours the recombinant plasmid pMAN1, described in FIG. 1 hereinafter. This vector contains the PCR fragment obtained above which is cloned into the SfrI site of the vector pPCR-Script (SK+). This cDNA was sequenced according to the "T7 sequencing kit" protocol (Amersham Pharmacia Biotech AB, SE-751 84 Uppsala, Sweden), in the presence of alpha ($^{35}$S)-DATP. The analysis of its sequence shows that it is located between nucleotides 743 and 1369 of the sequence SEQ ID NO: 1 and is bordered, at its 5' and 3' ends, by the respective sequences homologous to the oligonucleotide MAN2. By comparing with the protein sequence of *Trichoderma reesei* and *Aspergillus aculeatus* mannanase, it is deduced that the cDNA cloned in this way corresponds to a partial cDNA of the coffee endo-β-mannanase.

In order to isolate the full-length cDNA of the coffee endo-β-mannanase, a hybridization was carried out on colonies by testing 1800 transformants of *Escherichia coli* XL 2-Blue MRF' from the cDNA library, which hybridization was carried out on coffee beans undergoing germination.

Figure 2:
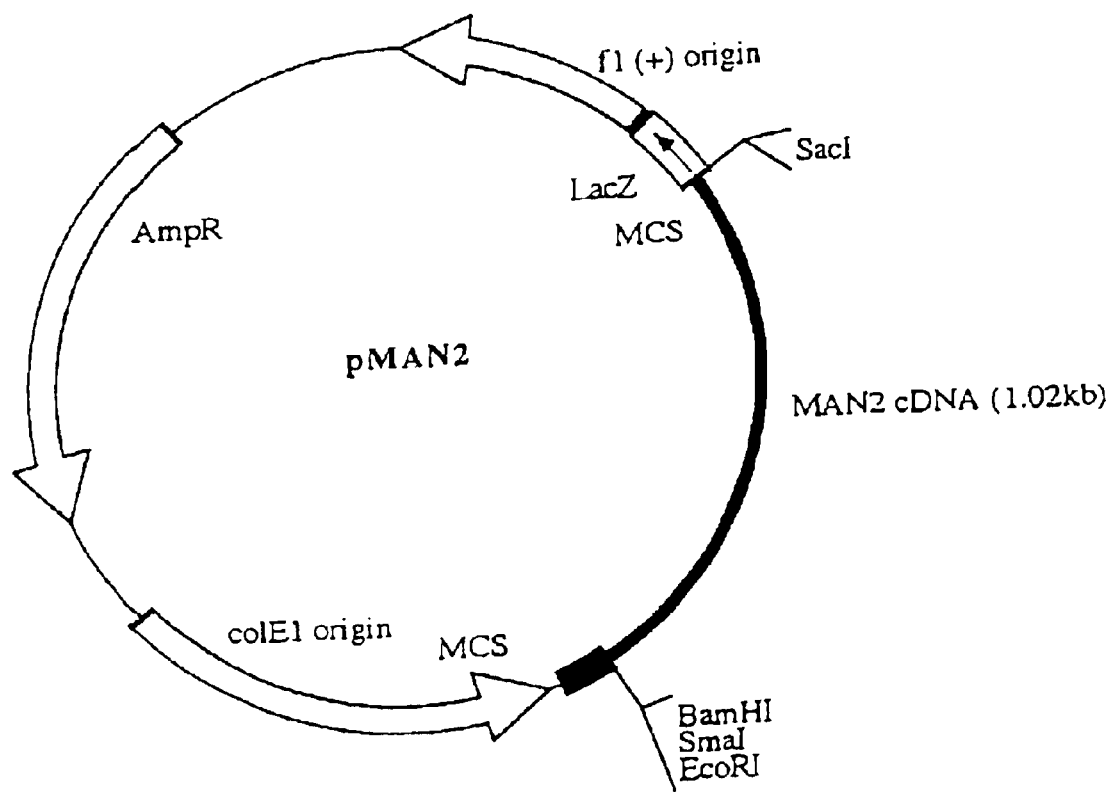
FIG. 2 represents the 2.98 kb plasmid pMAN2.

The transformants are transferred onto a Hybond N+ nylon filter (Amersham International plc., Amersham Place, Little Chalfont, Buckinghamshire HP7 9NA, UK) according to the suppliers' recommendations, and analysed by molecular hybridization with the MAN1 probe (50 ng). This probe is obtained after digesting the vector pMAN1 with the SmaI restriction enzyme. It was purified on electrophoresis gel and labelled by random primer extension with 50 µCi of alpha-($^{32}$P)-dCTP according to the protocol of the Megaprime kit (Amersham, UK). After hybridization, washing and autoradiography of the filters, a positive clone is detected which harbours the recombinant vector pMAN2, described in FIG. 2 hereinafter. This vector contains an approximately 1000 bp fragment of DNA, which was sequenced on both strands (Eurogentec Bel s.a.-Parc Scientifique du Sart Tilman [Sart Tilman Scientific Park]—4102 Seraing-Belgium). It comprises, in fact, the last 1022 base pairs of the sequence SEQ ID NO: 1, but again constitutes only a partial cDNA of the coffee endo-β-mannanase.

Figure 3:
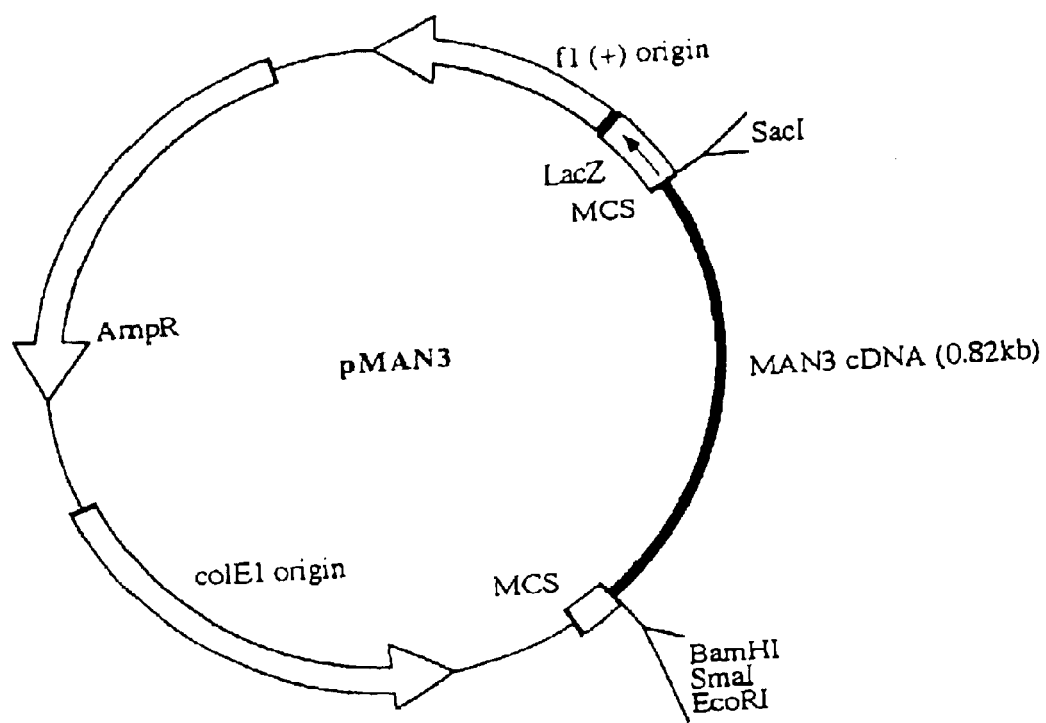
FIG. 3 represents the 3.78 kb plasmid pMAN3.

In order to isolate the 5' end of the coffee mannanase cDNA, a PCR reaction was carried out according to the conditions described above, but with the exception of the following parameters. 20 ng of the plasmid DNA library (22 DAS), the synthetic oligonucleotide MAN60, corresponding to the sequence SEQ ID NO. 5, and the universal oligonucleotides ForM13 and RevM13, which correspond to the sequences SEQ ID NO: 6 and SEQ ID NO: 7, respectively, were used. These primers are each located at approximately 100 bp on both sides of the SfrI cloning site of the vector pPCR-Script Amp SK (+). The primer MAN60 is, itself, located between nucleotides 803 and 819 of the sequence SEQ ID NO: 1. After this reaction, an approximately 900 bp amplification fragment [MAN60/ForM13] was obtained, which was digested with the SmaI restriction enzyme in order to eliminate the sequences of the plasmid pPCR-Script Amp SK (+). This digested DNA was ligated into the vector pPCR-Script Amp SK (+) so as to give the vector pMAN3 described in FIG. 3 hereinafter. The analysis of its sequence reveals that it corresponds to the 5' end of the cDNA encoding the coffee mannanase and that it is located between nucleotides 1 and 819 of the sequence SEQ ID NO: 1.

Since these experiments did not allow us to isolate a full length cDNA encoding the coffee mannanase, we decided to re-screen the plasmid DNA library (22 DAS), this time using the "ClonCapture cDNA Selection Kit" (Clontech Laboratories Inc., 1020 East Meadow Circle, Palo Alto Calif. 94303-4230 USA). In this case, the MAN3 probe, which is obtained by double digestion of the plasmid pMAN3 with the BamHI and SacI restriction enzymes, is used. This probe is biotinylated according to the protocol defined by Clontech (USA), and it is used to enrich the cDNA library in plasmid containing all or part of the sequences of the cDNA encoding the coffee mannanase. This enriched library was amplified in *Escherichia coli*, and was then screened using the MAN3 cDNA probe described above, which was labelled by random primer extension according to the protocol of the Megaprime kit (Amersham, UK).

Figure 4:
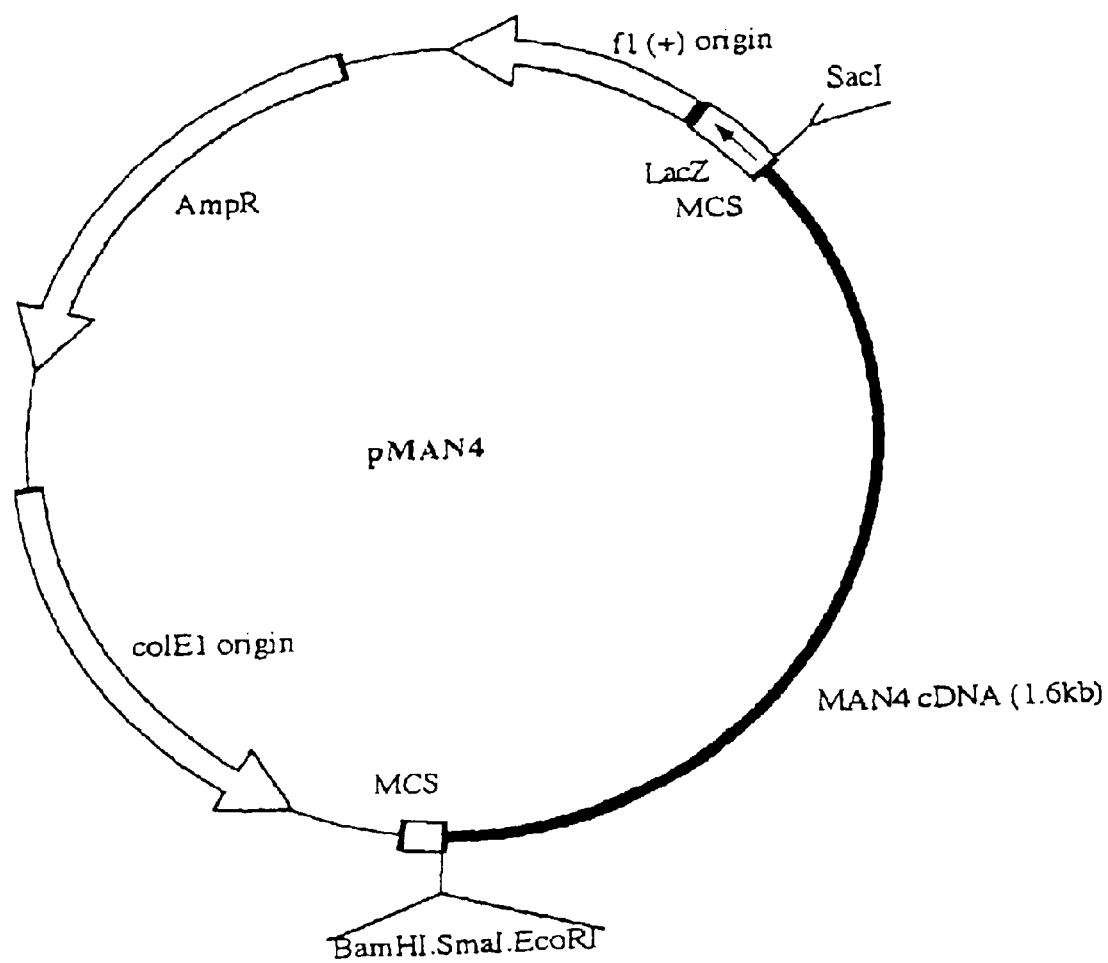
FIG. 4 represents the 4.56 kb plasmid pMAN4.

At the end of this screen, one positive clone in particular was selected, which contained an approximately 1600 bp cDNA cloned into the vector pPCR-Script Amp SK (+). This recombinant plasmid is named pMAN4, described in FIG. 4 hereinafter, and the cDNA which it harbours was sequenced. The analysis thereof in the Genbank databank (release 106.0) (Genetics Computer Group Inc., University Research Park, 575 Science Drive, Madison, Wis. 53711 USA) showed that it corresponds to the entire sequence SEQ ID NO: 1.

1.4. Analysis of the Full-length cDNA Encoding the Coffee Endo-β-mannanase

The analysis of the nucleic acid sequence shows that this full-length cDNA contains a short 10 bp transcribed, untranslated sequence at its 5' end, and a very long sequence (36 bp) corresponding to the poly A+ tail in the transcribed, untranslated 3' end of 280 bp. Within the latter sequence, an absence of AATAAA motifs which are presumed to be involved in polyadenylation mechanisms is observed, but, however, the presence of several nucleic acid motifs rich in GT (position) which might fulfil this role (Mogen et al., Plant Cell 2: 1261–1272, 1990) is noted.

Also noted are the presence of two inverted repeat sequences, which are very conserved between each other, and the existence of two large 34 bp direct repeat sequences, at position 1383–1417 and 1440–1474, which contain several repeats of the nucleic acid motif AGT(C/A)A(T)A) (G/A). The precise functions of these sequences are unknown, but it may be presumed that they are involved in mechanisms of stability of the messenger RNAs or of efficiency of translation, for example (Gallie, Plant Mol Biol, 32, 145–158, 1996).

The sequence SEQ ID NO: 1 contains an open reading frame of 428 codons, which begins with the ATG codon at position 11 and ends with a TGA codon (A at position 1294). The protein deduced from this complementary DNA has an approximate molecular weight of 48349 Da and has a very hydrophobic protein segment which corresponds to the first 30 amino acids of the sequence SEQ ID NO: 1. This protein sequence might correspond to a sequence of signal peptide type. In this case, the molecular weight of the protein is expected to be less than or equal to 45000 Da in its mature form.

The existence of several potential glycosylation sites (Asn/X/Ser or Thr) is also noted. The first two are located in the potential signal peptide, at position 8 and 11 of the sequence SEQ ID NO: 2, and are therefore presumed to be absent in the mature form of the mannanase. The other two are located at the C-terminal position, at position 389 and 412 of the sequence SEQ ID NO: 2.

Example 2

Measurement of the Peak of Activity of Endo-β-mannanase During Germination

Beans of the variety *Coffea arabica* var. *caturra* 2308 are harvested at the mature stage and treated as defined above during the isolation of the RNAs.

The batches of beans are harvested at various stages of germination (DAS 7, 14, etc), and then are ground in liquid nitrogen. Next, the powder is homogenized in a proportion of 1 g per 5 ml, in an extraction buffer (200/100 mM phosphate-citrate pH 5.0, 10 mM meta-bisulphite, $Na_2S_2O_5$, 5 mM EDTA and one tablet/50 ml of "Complete" protease inhibitor [Cat. No. 1836 145, Boehringer Mannheim, Mannheim, Germany]), for 20 min at 4° C. The homogenate is then centrifuged at 12 000 g for 20 min at 4° C., and the supernatant is recovered and centrifuged a second time. The supernatant, corresponding to the crude enzymatic extract, is then aliquoted and frozen at −80° C.

The enzymatic activity of the endo-β-mannanase is assayed according to the following method. A 400 µl crude enzymatic extract is added to 1.6 ml of reaction buffer (100 mM NaCl, 200 mM sodium acetate, pH 5.0) containing insoluble substrate (AZCL-Galactomannan, Megazyme, Co. Wicklow, Ireland) in a final quantity of 1% w/v. The reaction commences by adding the extract, and takes place at 37° C. with stirring. In order to calculate the initial slope of the reaction, a 400 µl aliquot of medium is removed every 15 min for 1 h, heated at 100° C. for 5 min and then centrifuged at 12 000 g for 2 min. The optical density of the supernatant is measured at 590 nm and the specific activity is expressed in AU (optical absorption units).$min^{-1}$.mg protein$^{-1}$, after having assayed the protein concentration in each extract by the Bradford method (Bradford, Anal. Biochem. 72, 248–254, 1976). Thus, it is found that the activity is virtually zero during the first 14 days after soaking (DAS), and subsequently increases gradually up to a maximum peak around 28 DAS. After 28 DAS, the activity slowly decreases.

Example 3

Endo-β-mannanase Purification Steps

According to the results described above, the purification strategy is continued using 16 ml of a 28-DAS crude enzyme extract having an activity of around 0.2 AU.$min^{-1}$.mg protein$^{-1}$×$10^{-2}$, a total protein content of approximately 48 mg and a total activity of 9.6 AU.$min^{-1}$×$10^-$.

3.1. Ammonium Sulphate Precipitation:

Initially, the crude enzymatic extract is fractionated by ammonium sulphate precipitation at 4° C. The ammonium sulphate is added slowly with stirring until a saturation level of 35% is obtained, and the solution is then centrifuged at 12 000 g at 4° C. for 20 min. The pellet thus obtained is taken up in a minimum (1 ml) of extraction buffer (see above). In this extract, the protein concentration is estimated at 11 mg.$ml^{-1}$. The endo-β-mannanase specific activity is 0.87 AU.$min^{-1}$.$mg^{-1}$×$10^{-2}$, which corresponds to a 4-fold enrichment of the enzyme with respect to the crude extract and a recovery of 10 AU.$min^{-1}$ [lacuna] of the total activity, i.e. 100%.

3.2. Separation on a Hydrophobic Interaction Column

The sample described above is then separated on a hydrophobic interaction column (Hiload HR 16/10 phenyl sepharose High performance, Amersham Pharmacia Biotech, Sweden). The column is pre-equilibrated with an equilibration buffer (50 mM sodium phosphate, 400 mM ammonium sulphate, pH 7.0). The sample (1 ml) is then injected onto the column, which is then washed with 5 column volumes of the equilibration buffer. A 0 to 99.5% gradient of water in 0.5 column volumes is applied, followed by another of 99.5 to 100% in 5 column volumes. The activity is mainly concentrated in three fractions, which are used to continue the purification. The purification yield of this step is 79% with respect to the previous step. The specific activity is 27 AU.$min^{-1}$.$mg^{-1}$ [lacuna], i.e. an approximately 137-fold enrichment with respect to the crude extract. The total activity recovered is approximately 9 AU.$min^{-1}$×$10^{-2}$, i.e. 90% of the initial activity.

3.3. Separation by Ion Exchange Chromatography

The three fractions described above are mixed and concentrated and the buffer changed using Ultrafree tubes (Millipore, Bedford, Mass., USA, centrifugation at 4 000 g maximum). The volume recovered is 1 ml. This sample is injected onto a Resource Q (Amersham Pharmacia Biotech AB SE-751 84 Uppsala, Sweden) anion exchange column pre-equilibrated with a 20 mM Tris/HCl, pH 8.0, buffer. The elution is carried out with a linear gradient of 0 to 1 M NaCl in 20 column volumes. The total activity recovered is present exclusively in two fractions. The purification yield of this step is 58% with respect to the previous step. The specific activity is 167 AU.$min^{-1}$.$mg^{-1}$ [lacuna], i.e. an approximately 836-fold enrichment with respect to the crude extract. The total activity recovered is 0.9 AU.$min^{-1}$ [lacuna], i.e. approximately 9% of the initial activity.

3.4. Separation by Gel Filtration Column

The two fractions recovered from the anion exchange column are concentrated to 100 µl by centrifugation at 4 000 g using the Ultrafree tubes (Millipore Co, 80 Ashby Road, Bedford, Mass., USA). This sample is injected onto a Superdex 75 HR 10/30 column (Amersham Pharmacia Biotech, Sweden) pre-equilibrated with a 50 mM sodium phosphate, 150 mM NaCl, pH 7.0, buffer. The proteins are eluted with the same buffer, with a flow rate of 0.3 ml.min$^{-1}$. A calibration curve for the column is prepared under the same conditions using molecular weight standards. The endo-[lacuna]-mannanase activity is distributed in two fractions, corresponding to a molecular weight of between 40 and 55 KDa. The purification yield of this final step is 48%. The specific activity is approximately 1 400 AU.min$^-$ 1.mg$^{-1}$ [lacuna], i.e. a 7 000-fold enrichment with respect to the crude extract. The total activity is 0.45 AU.min$^{-1}$ [lacuna], i.e. 4.5% of the initial activity.

3.5. Analyses by Bi-dimensional Electrophoresis and Microsequencing of the Amino Acids of the Purified Enzyme The fractions described above with the enzymatic activity at column exit are analysed during the purification by bi-dimensional electrophoreses. To do this, the fractions are mixed and concentrated to 20 µl by centrifugation in the Ultrafree tubes (Millipore, USA) as described above. 105 µl of rehydration buffer (8 M urea, 3% w/v CHAPS, 0.8% v/v ampholines, 1% w/v DTT) are added to this volume, and a non-linear (pH 3.0 to 10.0) 7 cm gel strip (Immobiline Dry Strip, Amersham Pharmacia Biotech, Sweden) is rehydrated according to the manufacturer's instructions. The proteins are then separated as a function of their isoelectric point (pI) using, for example, the IPGphore system (Amersham Pharmacia Biotech, Sweden) employing a total number of 14 000 volt-hours.

Following the separation of the proteins as a function of their pI, they are then separated in a second dimension according to their molecular weights. This separation is carried out according to the recommendations of Hochstrasser et al. (Anal. Biochem, 173, 412–423, 1989) and of Gorg et al. (Electrophoresis, 8, 122–124, 1987). Thus, the gel strip of the first dimension is equilibrated in a first solution (6 M urea, 30% v/v glycerol, 2% w/v SDS, 2% DTT, 50 mM Tris-HCl, pH 8.0) for 5 min, and then equilibrated in a second solution (6 M urea, 30% v/v glycerol, 2% w/v SDS, 2.5% w/v iodoacetamide, 50 mM Tris-HCl, pH 8.0) for 10 min. The gel strip is then loaded into a 10–20% acrylamide concentration gradient gel (dimensions 10×10×0.75 cm) with a single well, and covered with an agarose solution (1% w/v agarose, 0.5% w/v SDS, traces of bromophenol blue) pre-heated at 90° C. and maintained at 40° C. The gel is mounted in a vertical electrophoresis system and is subjected to a voltage of 170 V for 2 h. After migration, the proteins are stained with silver according to the method of Bjellqvist et al. (Electrophoresis, 14, 1357–1365, 1993). The profile of the mixture of the final three fractions thus obtained shows the presence of a single group of proteins which consist of a line of 5 proteins with the same approximate molecular weight of 48 kDa, but with slight differences in pI.

The proteins thus purified are analysed by microsequencing the amino acids. To do this, they are transferred onto a PVDF membrane ("Problot", Perkin Elmer Applied Biosystems, 850 Lincoln Centre Drive, Foster City, Calif. 94404, USA) using, for example, a Trans-Blot transfer cell (Bio-Rad, 2000 Alfred Drive, Hercules, Calif. 94547, USA). Thus, following the separation of the second dimension, the gel is recovered and shaken in a transfer solution (10% v/v methanol, 10 mM NaOH-CAPS, pH 11.0) for 10 min. During this time, two foam supports, two pieces of Whatman paper and a PVDF-Problot membrane (Perkin Elmer Applied Biosystem, USA) are wetted in the same solution. The gel, the membrane and the supports are mounted in the Trans-Blot system according to the manufacturer's (Bio-Rad, USA) instructions, and the transfer is carried out under a current of 100 V for one hour at a temperature of 4° C. At the end of the transfer, the proteins transferred onto the membrane are revealed with light Coomassie blue staining according to the instructions of the Problot membrane manufacturer. The various proteins are excised from the membrane, mixed and sequenced together. The N-terminal sequencing of the purified proteins and of the internal peptides is carried out with a Beckmann automatic sequencer (Beckmann Instruments Inc., 250 Harbor Boulevard Box 3100, Fullerton, Calif., 92634 USA) according to the methods described in Teixeira et al. (Electrophoresis, 18, 1491–1497).

Three sequences are obtained by this method; a 22-amino acid N-terminal sequence, called SEQ ID NO: 8, and two others concerning independent internal peptides, one having 10 amino acids (called SEQ ID NO: 9) and one having 17 amino acids (called 10) SEQ ID NO: 5. None of the sequences obtained have ambiguities and show that the 5 proteins, which make up the line described above, are isozymes of the endo-β-mannanase which share a sequence which is identical in the regions in question.

The three sequences SEQ ID NO: 8 to 10 have very strong homology with the sequence SEQ ID NO: 2. In particular, the sequence SEQ ID NO: 8 aligns with strong homology against amino acids 35 to 50 of SEQ ID NO: 2. This region corresponds exactly to the N-terminal sequence of the coffee bean endo-β-mannanase in its mature form, which begins just after a leader peptide corresponding to amino acids 1 to 34 of SEQ ID NO: 2. In addition, the internal sequences SEQ ID NO: 9 and SEQ ID NO: 10 align with very strong homology with the regions of SEQ ID NO: 2 corresponding to amino acids 93 to 102 and 259 to 275, respectively.

From the purification and microsequencing analysis described above, it may be concluded that the enzyme having the endo-β-mannanase activity in the coffee bean undergoing germination shares the same sequence as the protein described by the sequence SEQ ID NO: 2.

Example 4

Expression of the Coffee Mannanase in *Escherichia coli*

In order to overexpress and purify the coffee mannanase in *Escherichia coli*, a PCR amplification of the cDNA sequence between nucleotides 89 and 1313 of SEQ ID NO: 1 was carried out with the oligonucleotides TAM1 and TAM2 which have the sequences SEQ ID NO: 11 and 12, respectively. These two oligonucleotides make it possible to introduce unique BamHI and PstI sites into the PCR-amplified coffee sequence. They also make it possible to amplify the coffee DNA sequence which encodes the coffee mannanase but which lacks its cellular addressing sequence, called "signal peptide", which is between amino acids 1 and 26 of the sequence SEQ ID NO: 2. This strategy was followed in order to limit the toxic effects due to overexpression in *Escherichia coli* of the proteins which contain very hydrophobic sequences.

This reaction is carried out in the presence of 50 ng of vector pMAN4, in a final volume of 100 µl containing 1.5 units of Pwo DNA polymerase (Boehringer Mannheim), 10 µl of 10×Pwo DNA polymerase buffer (Boehringer Mannheim), 0.1 mM of each dNTP and 0.1 µM of each oligonucleotide (TAM1 and TAM2). The reaction mixture is incubated for 10 cycles (94° C.-30 S, 40° C.-60 s, 72° C.-2 min), followed by a final extension cycle at 72° C. for 7 min. 30 µl of the PCR mixture is then digested with the BamHI and PstI restriction enzymes, according to the recommendations supplied by Promega (USA).

The PCR-amplified fragment of coffee DNA (1231 bp) is separated by electrophoresis on 0.8% agarose gel and purified according to the recommendations supplied in the QIAquick Gel Extraction kit (Qiagen, USA). It is then ligated into the expression vector pQE31 (Qiagen, USA) digested with the BamHI and PstI enzymes and dephosphorylated by calf intestin alkaline phosphatase treatment, beforehand. The use of the expression vector pQE31 makes it possible to introduce 6 histidines (6 His tag) in frame with the N-terminal end of the coffee mannanase, which then enables this recombinant protein to be purified after it has been passed over a column of Ni-NTA resin containing $Ni^{2+}$ ions (Hochuli et al., J. Chromatography, 411, 177–184, 1987).

The ligation mixture was used to transform competent cells of the *Escherichia coli* strain M15[pREP4], according to the recommendations supplied by Qiagen (USA), and the recombinant bacteria were selected on dishes of LB medium containing 25 µg.ml$^{-1}$ of kanamycin and 100 µg.ml$^{-1}$ of ampicillin.

In order to test the expression of coffee mannanase in *Escherichia coli*, the bacteria are then cultured in 50 ml of liquid LB medium supplemented with the antiobiotics as indicated above, until an OD at 600 nm=1 is obtained. The induction is carried out by adding IPTG (final concentration 1 mM) to the culture medium, and culture samples are taken every 30 min. The bacteria are lysed and the soluble *Escherichia coli* proteins are extracted under denaturing conditions and separated on a column of Ni-NTA resin following the protocol defined by QIAGEN (QIAexpress system). The successively eluted protein fractions were then analysed by SDS-PAGE electrophoresis. We were thus able to show that the only protein capable of attaching to the Ni-NTA column corresponds to the coffee mannanase. This protein is expressed in *Escherichia coli* in an approximate molecular weight of 45 kDa, which is in agreement with that observed by electrophoresis on the purified fractions of the mannanase obtained from the beans undergoing germination at 28 DAS, this taking into account the protein sequence modifications which were produced during the construction of the expression vector.

What is claimed is:

1. An isolated nucleic acid molecule comprising a nucleic acid molecule isolated from coffee encoding at least one enzyme that hydrolyzes polysaccharides having pure or branched mannan molecules linked to each other via a β (1→4) linkage, wherein the enzyme is a peptide comprising SEQ ID NO:2.

2. A fragment of an isolated nucleic acid molecule from coffee encoding at least one enzyme that hydrolyzes polysaccharides comprising pure or branched mannan molecules linked to each other via a β (1→4) linkage, comprising nucleotides 11 to 1294 of the nucleic acid sequence SEQ ID NO:1.

3. The nucleic acid molecule according to claim 2, comprising the nucleic acid sequence SEQ ID NO:1.

4. An isolated nucleic acid molecule having at least 90% homology with nucleic acid sequence SEQ ID NO:1, wherein the nucleic acid molecule is isolated from coffee and encodes at least one enzyme that hydrolyzes polysaccharides having pure or branched mannan molecules linked to each other via a β (1→4) linkage.

5. A recombinant vector comprising an isolated nucleic acid molecule that encodes at least one enzyme that hydrolyzes polysaccharides having pure or branched mannan molecules linked to each other via a β (1→4) linkage, wherein the enzyme is a peptide comprising SEQ ID NO:2.

6. A microorganism comprising an isolated nucleic acid molecule, or fragment thereof, encoding at least one enzyme that hydrolyzes polysaccharides comprising pure or branched mannan molecules linked to each other via a β (1→4) linkage, wherein the enzyme is a peptide comprising SEQ ID NO:2 and the isolated nucleic acid and molecule, or fragment thereof is integrated into the genome or plasmid of said microorganism, wherein said fragment comprises nucleotides 11 to 1294 of SEQ ID NO:1.

7. The microorganism according to claim 6, wherein the isolated nucleic acid molecule has at least 90% homology with SEQ ID NO:1.

8. The nucleic acid molecule of claim 1, wherein the nucleic acid molecule has at least 90% homology with SEQ ID NO:1.

9. The nucleic acid molecule of claim 8, wherein the nucleic acid molecule is SEQ ID NO:1 or nucleotides 11 to 1294 of the nucleic acid sequence SEQ ID NO:1.

10. The nucleic acid molecule of claim 4, wherein the nucleic acid molecule is SEQ ID NO:1 or nucleotides 11 to 1294 of the nucleic acid sequence SEQ ID NO:1.

11. A recombinant vector comprising an isolated nucleic acid molecule according to claim 4.

12. The recombinant vector of claim 5, wherein the nucleic acid molecule is SEQ ID NO:1 or nucleotides 11 to 1294 of the nucleic acid sequence SEQ ID NO:1.

13. The microorganism of claim 7, wherein the nucleic acid molecule is SEQ ID NO:1 or nucleotides 11 to 1294 of the nucleic acid sequence SEQ ID NO:1.

* * * * *